United States Patent [19]
Eda et al.

[11] Patent Number: 5,712,373
[45] Date of Patent: Jan. 27, 1998

[54] HIV MONOCLONAL ANTIBODY SPECIFIC FOR THE HTLV-III$_{MN}$ GP120 ENVELOPE GLYCOPROTEIN

[75] Inventors: Yasuyuki Eda, Kumamoto-ken; Kiyoshi Osatomi, Nagasaki; Kouichi Shiosaki, Kumamoto-ken; Sachio Tokiyoshi; Shuzo Matsushita, both of Kumamoto; Toshio Hattori, Kyoto; Kiyoshi Takatsuki, Kumamoto, all of Japan

[73] Assignee: Juridical Foundation The Chemo-Sero-Therapeutic Research Institute, Kumamoto, Japan

[21] Appl. No.: 253,030

[22] Filed: Jun. 2, 1994

Related U.S. Application Data

[63] Continuation-in-part of Ser. No. 723,916, Jul. 1, 1991, abandoned.

[30] Foreign Application Priority Data

| | | | |
|---|---|---|---|
| Jul. 2, 1990 | [JP] | Japan | 2-175075 |
| Jul. 16, 1990 | [JP] | Japan | 2-188300 |

[51] Int. Cl.$^6$ .............................. C07K 16/10; C12N 5/20
[52] U.S. Cl. .................. 530/388.35; 435/240.27
[58] Field of Search ............... 530/388.35, 389.4; 435/240.27, 172.2, 70.21

[56] References Cited

FOREIGN PATENT DOCUMENTS

| | | |
|---|---|---|
| 0339504 | 11/1989 | European Pat. Off. |
| WO8809181 | 12/1988 | WIPO |
| WO9003984 | 4/1990 | WIPO |
| WO9015078 | 12/1990 | WIPO |

OTHER PUBLICATIONS

R.A. Weiss et al., Nature, 316 (1985), pp. 69–72.
L.A. Lasky et al., Science, 233 (1986), pp. 209–212.
J.S. McDougal et al., Science, 231 (1986), pp. 382–385.
J.D. Lifson et al., Nature, 323 (1986), pp. 725–728.
F.D. Veronese et al., Proc.Nat'l.Acad.Sci.USA, 82 (1985), pp. 5199–5202.
F.D. Veronese et al., Science, 231 (1986), pp. 1289–1291.
F.D. Veronese et al., Science, 229 (1985), pp. 1402–1405.
J. Chassagne et al., J.Immunol. 136 (1986), pp. 1442–1445.
T.C. Chanh et al., Eur. J. Immunol., 16 (1986), pp. 1465–1468.
S. Matsushita et al., J. Virology, 62 (1988), pp. 2107–2114.
G. Köhler & C. Milstein, Nature, 256 (1975), p. 495.
M. Shulman et al., Nature, 276 (1978), p. 269.
G. Köhler & C. Milstein, Eur. J. Immunol., 6, (1976), p. 511.
J.F. Kearney et al., J.Immunol., 123 (1979), p. 1548.
G. Bressan & K. Stanley, Nucleic Acid Research, 15 (1987), p. 10056.
H. Towbin et al., Proc.Nat'l.Acad.Sci.USA, 76 (1979), p. 4350.
M. Ropovic et al., Science, 224 (1984), p. 497.
Robinson et al., Aids Research and Human Retroviruses 6(5): 567–579, May 1990.
Fahey et al., Clin. Exp. Immunol., 88 (1992), pp. 1–5.
Y.Kim et al., "Immunoconjugates That Neutralize HIV Virons Kill T–Cells Infected with Diverse Strains of HIV–1$^1$", J.Immun., vol. 144, No. 4 (Feb. 15, 1990), pp. 1257–1262.
A. Profy et al., "Epitopes Recognized By The Neutralizing Antibodies of an HIV–1–Infected Individual", J.Immun., vol. 144, No. 12 (Jun. 15, 1990), pp. 4641–4647.
T. Palker et al., "Polyvalent Human Immunodeficiency Virus Synthetic Immunogen Comprised of Envelope gp120 T Helper Cell Sites and B Cell Neutralization Epitopes", J.Immun., vol. 142, No. 10 (May 1989), pp.3612–3619.
Y. Devash et al., "C–Terminal Fragments of gp120 and Synthetic Peptides From Five HTLV–III Strains . . . ", Aids Research and Human Retroviruses, vol. 6, No. 3 (1990), pp. 307–316.

*Primary Examiner*—Paula K. Hutzell
*Attorney, Agent, or Firm*—Foley & Lardner

[57] ABSTRACT

A murine monoclonal antibody which specifically binds to a glycoprotein antigen having a molecular weight of about $12 \times 10^4$ daltons (gp120) present in the envelope of human T-lymphotropic virus III$_{MN}$ (HTLV-III$_{MN}$) and capable of neutralizing the HTLV-III$_{MN}$ as determined by in vitro inhibition of syncytium formation but does not bind to other HTLV-III strains, or antigen-binding fragments, which is useful for prophylaxis, treatment and diagnosis of AIDS.

1 Claim, 5 Drawing Sheets

Dilution of Antibody

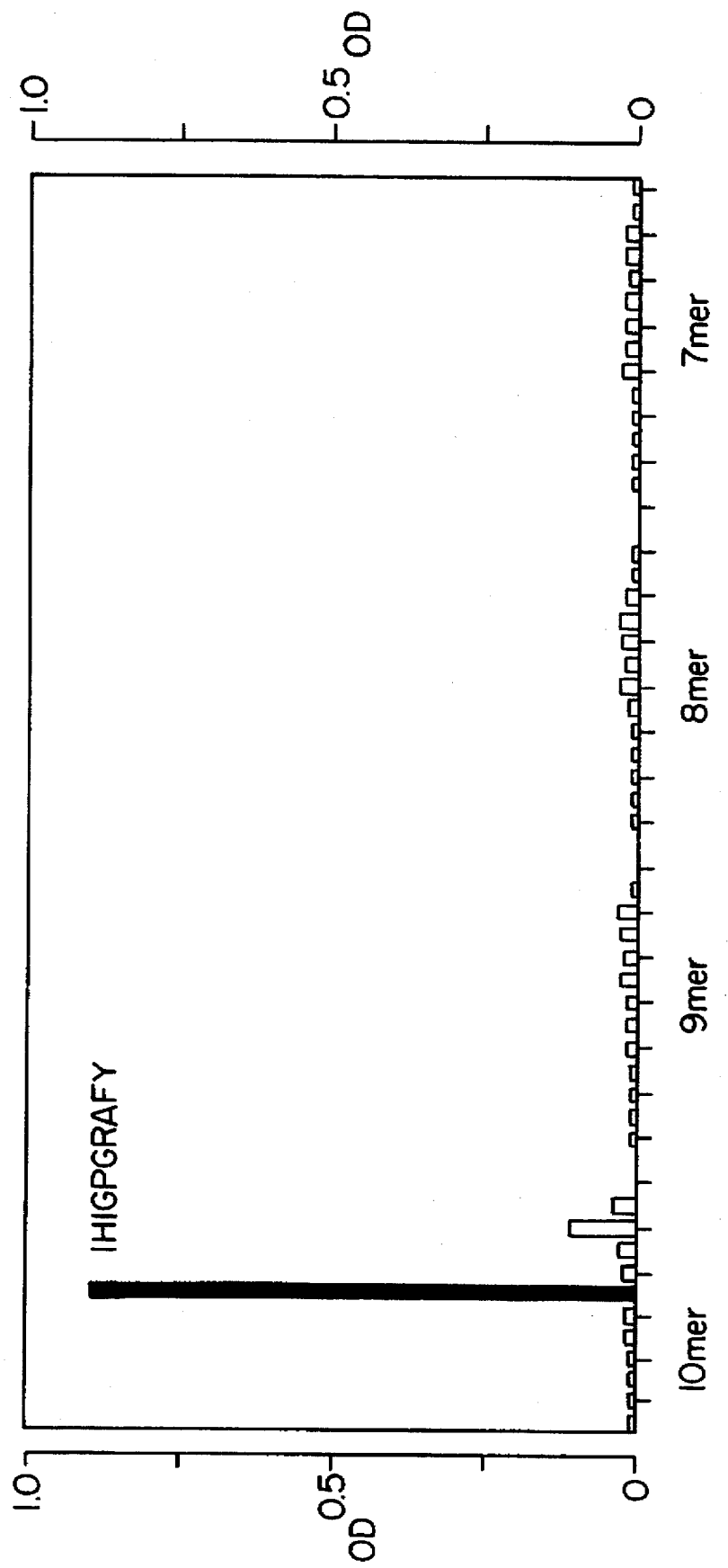

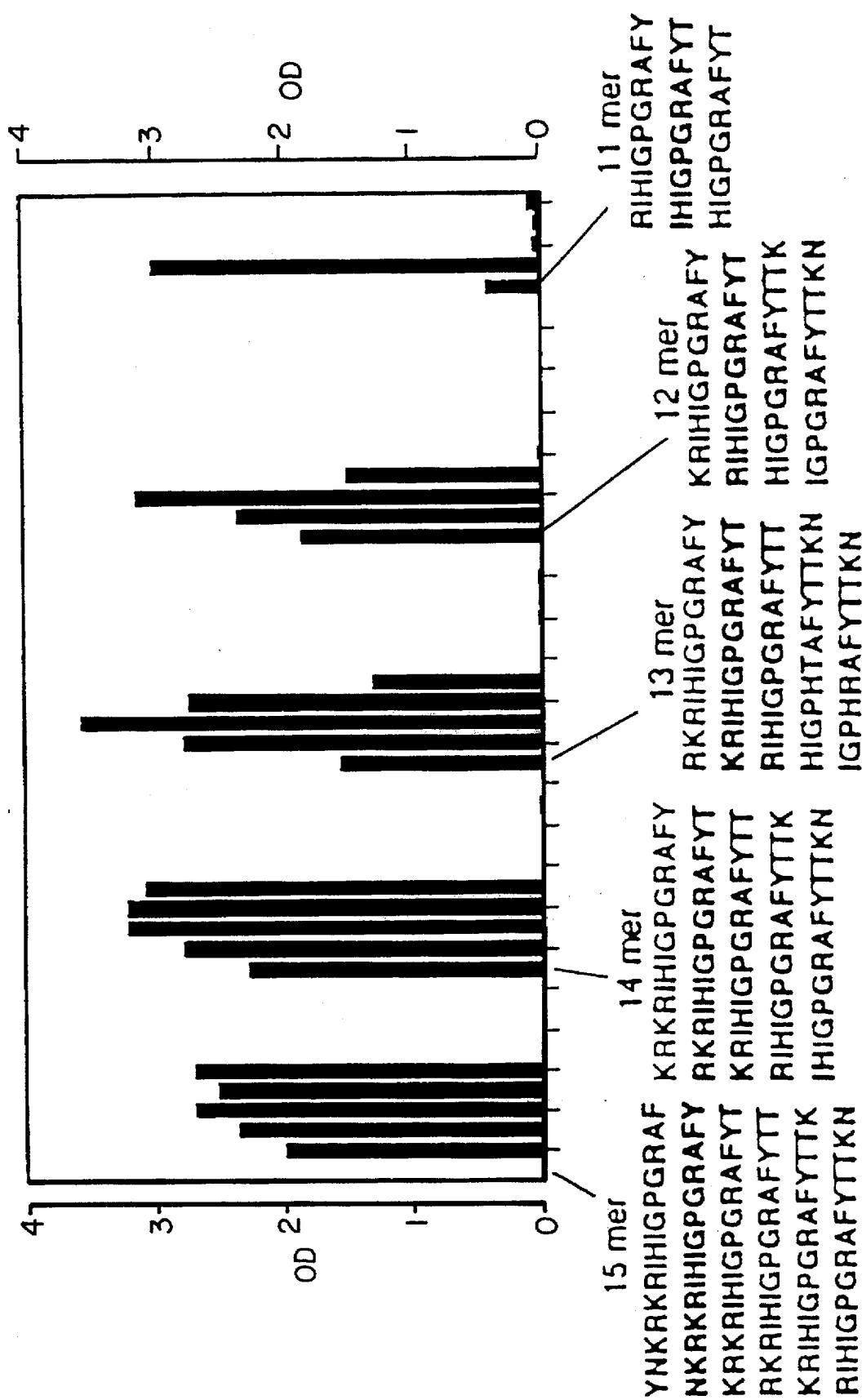

SEQUENCE LISTING ( 1 ) GENERAL INFORMATION:

( i i i ) NUMBER OF SEQUENCES: 30

( 2 ) INFORMATION FOR SEQ ID NO:1:

( i ) SEQUENCE CHARACTERISTICS:
       ( A ) LENGTH: 15 amino acids
       ( B ) TYPE: amino acid
       ( C ) STRANDEDNESS:
       ( D ) TOPOLOGY: linear ( x i ) SEQUENCE DESCRIPTION: SEQ ID NO:1:

Tyr Asn Lys Arg Lys Arg Ile His Ile Gly Pro Gly Arg Ala Phe
   1               5                   10                  15

( 2 ) INFORMATION FOR SEQ ID NO:2:

( i ) SEQUENCE CHARACTERISTICS:
       ( A ) LENGTH: 15 amino acids
       ( B ) TYPE: amino acid
       ( C ) STRANDEDNESS:
       ( D ) TOPOLOGY: linear ( x i ) SEQUENCE DESCRIPTION: SEQ ID NO:2:

Asn Lys Arg Lys Arg Ile His Ile Gly Pro Gly Arg Ala Phe Tyr
   1               5                   10                  15

( 2 ) INFORMATION FOR SEQ ID NO:3:

( i ) SEQUENCE CHARACTERISTICS:
       ( A ) LENGTH: 15 amino acids
       ( B ) TYPE: amino acid
       ( C ) STRANDEDNESS:
       ( D ) TOPOLOGY: linear ( x i ) SEQUENCE DESCRIPTION: SEQ ID NO:3:

Lys Arg Lys Arg Ile His Ile Gly Pro Gly Arg Ala Phe Tyr Thr
   1               5                   10                  15

( 2 ) INFORMATION FOR SEQ ID NO:4:

( i ) SEQUENCE CHARACTERISTICS:
       ( A ) LENGTH: 15 amino acids
       ( B ) TYPE: amino acid
       ( C ) STRANDEDNESS:
       ( D ) TOPOLOGY: linear ( x i ) SEQUENCE DESCRIPTION: SEQ ID NO:4:

Arg Lys Arg Ile His Ile Gly Pro Gly Arg Ala Phe Tyr Thr Thr
   1               5                   10                  15

( 2 ) INFORMATION FOR SEQ ID NO:5:

( i ) SEQUENCE CHARACTERISTICS:
       ( A ) LENGTH: 15 amino acids
       ( B ) TYPE: amino acid
       ( C ) STRANDEDNESS:
       ( D ) TOPOLOGY: linear ( x i ) SEQUENCE DESCRIPTION: SEQ ID NO:5:

Lys Arg Ile His Ile Gly Pro Gly Arg Ala Phe Tyr Thr Thr Lys
   1               5                   10                  15

( 2 ) INFORMATION FOR SEQ ID NO:6:

(i) SEQUENCE CHARACTERISTICS:
(A) LENGTH: 15 amino acids
(B) TYPE: amino acid
(C) STRANDEDNESS:
(D) TOPOLOGY: linear (xi) SEQUENCE DESCRIPTION: SEQ ID NO:6:

Arg Ile His Ile Gly Pro Gly Arg Ala Phe Tyr Thr Thr Lys Asn
1               5                   10                  15

(2) INFORMATION FOR SEQ ID NO:7:

(i) SEQUENCE CHARACTERISTICS:
(A) LENGTH: 14 amino acids
(B) TYPE: amino acid
(C) STRANDEDNESS:
(D) TOPOLOGY: linear (xi) SEQUENCE DESCRIPTION: SEQ ID NO:7:

Lys Arg Lys Arg Ile His Ile Gly Pro Gly Arg Ala Phe Tyr
1               5                   10

(2) INFORMATION FOR SEQ ID NO:8:

(i) SEQUENCE CHARACTERISTICS:
(A) LENGTH: 14 amino acids
(B) TYPE: amino acid
(C) STRANDEDNESS:
(D) TOPOLOGY: linear (xi) SEQUENCE DESCRIPTION: SEQ ID NO:8:

Arg Lys Arg Ile His Ile Gly Pro Gly Arg Ala Phe Tyr Thr
1               5                   10

(2) INFORMATION FOR SEQ ID NO:9:

(i) SEQUENCE CHARACTERISTICS:
(A) LENGTH: 14 amino acids
(B) TYPE: amino acid
(C) STRANDEDNESS:
(D) TOPOLOGY: linear (xi) SEQUENCE DESCRIPTION: SEQ ID NO:9:

Lys Arg Ile His Ile Gly Pro Gly Arg Ala Phe Tyr Thr Thr
1               5                   10

(2) INFORMATION FOR SEQ ID NO:10:

(i) SEQUENCE CHARACTERISTICS:
(A) LENGTH: 14 amino acids
(B) TYPE: amino acid
(C) STRANDEDNESS:
(D) TOPOLOGY: linear (xi) SEQUENCE DESCRIPTION: SEQ ID NO:10:

Arg Ile His Ile Gly Pro Gly Arg Ala Phe Tyr Thr Thr Lys
1               5                   10

(2) INFORMATION FOR SEQ ID NO:11:

(i) SEQUENCE CHARACTERISTICS:
(A) LENGTH: 14 amino acids
(B) TYPE: amino acid
(C) STRANDEDNESS:
(D) TOPOLOGY: linear (xi) SEQUENCE DESCRIPTION: SEQ ID NO:11:

Ile His Ile Gly Pro Gly Arg Ala Phe Tyr Thr Thr Lys Asn
1               5                   10

( 2 ) INFORMATION FOR SEQ ID NO:12:

( i ) SEQUENCE CHARACTERISTICS:
        ( A ) LENGTH: 13 amino acids
        ( B ) TYPE: amino acid
        ( C ) STRANDEDNESS:
        ( D ) TOPOLOGY: linear ( x i ) SEQUENCE DESCRIPTION: SEQ ID NO:12:

```
Arg Lys Arg Ile His Ile Gly Pro Gly Arg Ala Phe Tyr
 1               5                  10
```

( 2 ) INFORMATION FOR SEQ ID NO:13:

( i ) SEQUENCE CHARACTERISTICS:
        ( A ) LENGTH: 13 amino acids
        ( B ) TYPE: amino acid
        ( C ) STRANDEDNESS:
        ( D ) TOPOLOGY: linear ( x i ) SEQUENCE DESCRIPTION: SEQ ID NO:13:

```
Lys Arg Ile His Ile Gly Pro Gly Arg Ala Phe Tyr Thr
 1               5                  10
```

( 2 ) INFORMATION FOR SEQ ID NO:14:

( i ) SEQUENCE CHARACTERISTICS:
        ( A ) LENGTH: 13 amino acids
        ( B ) TYPE: amino acid
        ( C ) STRANDEDNESS:
        ( D ) TOPOLOGY: linear ( x i ) SEQUENCE DESCRIPTION: SEQ ID NO:14:

```
Arg Ile His Ile Gly Pro Gly Arg Ala Phe Tyr Thr Thr
 1               5                  10
```

( 2 ) INFORMATION FOR SEQ ID NO:15:

( i ) SEQUENCE CHARACTERISTICS:
        ( A ) LENGTH: 13 amino acids
        ( B ) TYPE: amino acid
        ( C ) STRANDEDNESS:
        ( D ) TOPOLOGY: linear ( x i ) SEQUENCE DESCRIPTION: SEQ ID NO:15:

```
His Ile Gly Pro His Thr Ala Phe Tyr Thr Thr Lys Asn
 1               5                  10
```

( 2 ) INFORMATION FOR SEQ ID NO:16:

( i ) SEQUENCE CHARACTERISTICS:
        ( A ) LENGTH: 12 amino acids
        ( B ) TYPE: amino acid
        ( C ) STRANDEDNESS:
        ( D ) TOPOLOGY: linear ( x i ) SEQUENCE DESCRIPTION: SEQ ID NO:16:

```
Ile Gly Pro His Arg Ala Phe Tyr Thr Thr Lys Asn
 1               5                  10
```

( 2 ) INFORMATION FOR SEQ ID NO:17:

( i ) SEQUENCE CHARACTERISTICS:
        ( A ) LENGTH: 12 amino acids
        ( B ) TYPE: amino acid
        ( C ) STRANDEDNESS:
        ( D ) TOPOLOGY: linear (x i) SEQUENCE DESCRIPTION: SEQ ID NO:17:

Lys Arg Ile His Ile Gly Pro Gly Arg Ala Phe Tyr
1               5                       10

(2) INFORMATION FOR SEQ ID NO:18:

(i) SEQUENCE CHARACTERISTICS:
      (A) LENGTH: 12 amino acids
      (B) TYPE: amino acid
      (C) STRANDEDNESS:
      (D) TOPOLOGY: linear (x i) SEQUENCE DESCRIPTION: SEQ ID NO:18:

Arg Ile His Ile Gly Pro Gly Arg Ala Phe Tyr Thr
1               5                       10

(2) INFORMATION FOR SEQ ID NO:19:

(i) SEQUENCE CHARACTERISTICS:
      (A) LENGTH: 12 amino acids
      (B) TYPE: amino acid
      (C) STRANDEDNESS:
      (D) TOPOLOGY: linear (x i) SEQUENCE DESCRIPTION: SEQ ID NO:19:

His Ile Gly Pro Gly Arg Ala Phe Tyr Thr Thr Lys
1               5                       10

(2) INFORMATION FOR SEQ ID NO:20:

(i) SEQUENCE CHARACTERISTICS:
      (A) LENGTH: 12 amino acids
      (B) TYPE: amino acid
      (C) STRANDEDNESS:
      (D) TOPOLOGY: linear (x i) SEQUENCE DESCRIPTION: SEQ ID NO:20:

Ile Gly Pro Gly Arg Ala Phe Tyr Thr Thr Lys Asn
1               5                       10

(2) INFORMATION FOR SEQ ID NO:21:

(i) SEQUENCE CHARACTERISTICS:
      (A) LENGTH: 11 amino acids
      (B) TYPE: amino acid
      (C) STRANDEDNESS:
      (D) TOPOLOGY: linear (x i) SEQUENCE DESCRIPTION: SEQ ID NO:21:

Arg Ile His Ile Gly Pro Gly Arg Ala Phe Tyr
1               5                       10

(2) INFORMATION FOR SEQ ID NO:22:

(i) SEQUENCE CHARACTERISTICS:
      (A) LENGTH: 11 amino acids
      (B) TYPE: amino acid
      (C) STRANDEDNESS:
      (D) TOPOLOGY: linear (x i) SEQUENCE DESCRIPTION: SEQ ID NO:22:

Ile His Ile Gly Pro Gly Arg Ala Phe Tyr Thr
1               5                       10

(2) INFORMATION FOR SEQ ID NO:23:

(i) SEQUENCE CHARACTERISTICS:
      (A) LENGTH: 10 amino acids (B) TYPE: amino acid
(C) STRANDEDNESS:
(D) TOPOLOGY: linear (xi) SEQUENCE DESCRIPTION: SEQ ID NO:23:

His Ile Gly Pro Gly Arg Ala Phe Tyr Thr
1               5                   10

(2) INFORMATION FOR SEQ ID NO:24:

(i) SEQUENCE CHARACTERISTICS:
(A) LENGTH: 23 amino acids
(B) TYPE: amino acid
(C) STRANDEDNESS:
(D) TOPOLOGY: linear (xi) SEQUENCE DESCRIPTION: SEQ ID NO:24:

Tyr Asn Lys Arg Lys Arg Ile His Ile Gly Pro Gly Arg Ala Phe Tyr
1               5                   10                  15

Thr Thr Lys Asn Ile Ile Gly
            20

(2) INFORMATION FOR SEQ ID NO:25:

(i) SEQUENCE CHARACTERISTICS:
(A) LENGTH: 10 amino acids
(B) TYPE: amino acid
(C) STRANDEDNESS:
(D) TOPOLOGY: linear (xi) SEQUENCE DESCRIPTION: SEQ ID NO:25:

Ile His Ile Gly Pro Gly Arg Ala Phe Tyr
1               5                   10

(2) INFORMATION FOR SEQ ID NO:26:

(i) SEQUENCE CHARACTERISTICS:
(A) LENGTH: 22 base pairs
(B) TYPE: nucleic acid
(C) STRANDEDNESS: single
(D) TOPOLOGY: linear (xi) SEQUENCE DESCRIPTION: SEQ ID NO:26:

TGTACACATG GAATTAGGCC AG                                     22

(2) INFORMATION FOR SEQ ID NO:27:

(i) SEQUENCE CHARACTERISTICS:
(A) LENGTH: 22 base pairs
(B) TYPE: nucleic acid
(C) STRANDEDNESS: single
(D) TOPOLOGY: linear (iv) ANTI-SENSE: YES (xi) SEQUENCE DESCRIPTION: SEQ ID NO:27:

ATTTCTGGGT CCCCTCCTGA AG                                     22

(2) INFORMATION FOR SEQ ID NO:28:

(i) SEQUENCE CHARACTERISTICS:
(A) LENGTH: 28 base pairs
(B) TYPE: nucleic acid
(C) STRANDEDNESS: single
(D) TOPOLOGY: linear (xi) SEQUENCE DESCRIPTION: SEQ ID NO:28:

ATAATCCACC TATCCCAGTA GGAGAAAT                               28

(2) INFORMATION FOR SEQ ID NO:29:

(i) SEQUENCE CHARACTERISTICS:
(A) LENGTH: 28 base pairs
(B) TYPE: nucleic acid
(C) STRANDEDNESS: single
(D) TOPOLOGY: linear (xi) SEQUENCE DESCRIPTION: SEQ ID NO:29:

TTTGGTCCTT GTCTTATGTC CAGAATGC    28

(2) INFORMATION FOR SEQ ID NO:30:

(i) SEQUENCE CHARACTERISTICS:
(A) LENGTH: 41 base pairs
(B) TYPE: nucleic acid
(C) STRANDEDNESS: single
(D) TOPOLOGY: linear (xi) SEQUENCE DESCRIPTION: SEQ ID NO:30:

ATCCTGGGAT TAAATAAAAT AGTAAGAATG TATAGCCCTA C    41

HIV MONOCLONAL ANTIBODY SPECIFIC FOR THE HTLV-III$_{MN}$ GP120 ENVELOPE GLYCOPROTEIN

This application is a continuation-in-part application of U.S. Ser. No. 07/723,916 filed on Jul. 1 1991 (now abandoned).

This invention relates to an immunological technology providing a novel substance for the prophylaxis, treatment and diagnosis of virus infectious diseases. More particularly, it relates to a monoclonal antibody being capable of neutralizing human immunodeficiency virus (abbreviated as HIV) which is the etiologic agent of the acquired immunodeficiency syndrome (abbreviated as AIDS), and to a hybridoma being capable of secreting the monoclonal antibody.

TECHNICAL BACKGROUND AND PRIOR ART

HIV is a retrovirus which is known to be cause of diseases such as AIDS and AIDS-related complex (abbreviated as ARC). It is well known that proto-type HIV includes human T-lymphotropic virus type III (abbreviated as HTLV-III) and lymphadenopathy associated virus (abbreviated as LAV). The above diseases are one of the recent most serious problems in the world, and it has been desired to develope a vaccine or a therapeutic method for the treatment thereof, but there has never been found any effective means. The most characteristic hemotological anomaly in AIDS is functional and quantitative loss of helper/inducer T lymphocyte having CD4 antigen on the surface thereof. The immunodeficiency caused by HIV induces various disorders in the bio-phylactic mechanism in the infected host (human), and then highly frequently induces opportunistic infections such as *Pneumocystis carinii* pneumonia and unusual malignant tumors such as Kaposi's sarcoma. The immunodeficiency caused by HIV is a progressive and irreversible disease with high death rate, and it is considered that the death rate of the disease will reach 100% within several years.

In case of infection of HIV to T cell with virus particles, the virus particles will first bind to the receptor CD4 antigen. The infection of HIV also spreads via cell-to-cell infection. That is, infected cells are cell-fused with non-infected cells, and particularly in organs such as brain, lymphonodus, etc., syncytium (macropolycyte) is formed. The syncytium formation is also observed in experiment in vitro. It is usually considered that the T cells infected with HIV are easily suffered from cytopathic effect of HIV and this will cause the loss of CD4-positive cell.

It is also known that HIV infects not only the helper/inducer T lymphocytes but also monocyte/macrophages and further that most monocyte/macrophages and a part of the T lymphocytes have resistance to the cytopathic effect of HIV and hence these cells retain The virus for a long period of time and continuously produce the virus.

Moreover, it is known that human blood serum infected by HIV contains an antibody to HIV, but the antibody has merely low neutralizing activity (cf. Weiss et al., Nature, 316, p.69–72, 1985).

It is well known that a core antigen (gag) and an envelope antigen are present as the structural protein antigen of HIV. The HIV viral envelope protein is expressed as a precursor glycoprotein having a molecular weight of 160 kilodaltons (gp160) that is proteolytically cleaved to generate an external envelope glycoproteins having a molecular weight of 120 kilodaltons (gp120) and a trans-membrane envelope glycoprotein having a molecular weight of 41 kilodaltons (gp41). Among these, gp120 is the most important by the following reasons.

(1) When a test animal is infected with the gp120 or with a certain fragment derived from the gp120, a polyclonal neutralizing antibody is produced. This means that the gp120 is at least one of the target molecules of an antibody capable of neutralizing the virus (cf. Lasky et al., Science, 233, p.209–212, 1986).

(2) At the first step of infection of HIV, the gp120 binds to CD4 molecule of virus receptor. This means that the gp120 is the most important molecule as to the HIV infection (McDougal et al., Science 231, p.382–385, 1986).

(3) The syncytium formation by HIV, that is cell-to-cell infection of HIV, is induced by the direct interaction between the gp120 and the CD4 molecule of non-infected cells (cf. Lifson et al., Nature, 323, p.725–728, 1985).

Various monoclonal antibodies to constructive proteins of HTLV-III or LAV have been known, for example, antibody against p24 which is one of core antigens present within virus (Veronese, F. D., Proc. Natl. Acad. Sci., U.S.A., 82, p.5199–5202, 1985); antibody to pol gene product encoding a reverse transcriptase of virus (Veronese, F. D., Science, 231, p.1289–1291, 1986); and antibody to gp41 which is another constructive protein in the envelope (Veronese, F. D., Science, 229, p.1402–1405, 1985). However, none of these known monoclonal antibodies does react with the gp120 antigen which is an important factor for the prophylaxis and treatment of AIDS. It is rather reported that any monoclonal antibody being capable of effectively neutralizing the gp120 antigen could not be obtained even by immunizing animals with a purified LAV (Chassange, J. et al., J. Immunol., 136, p.1442–1445, 1985).

There have hitherto been studied various methods for obtaining monoclonal antibody being capable of effectively neutralizing AIDS virus and hence being useful for the prophylaxis, treatment and diagnosis of AIDS.

It is reported that a monoclonal antibody to the gp120 antigen has been obtained by using a synthetic peptide as an immunogen and that an epitope recognized by the antibody is within the region of the amino acid sequence 503–532 of the HIV envelope (Chanh, T. C. et al., Eur. J. Immunol., 16, p.1455–1468, 1986). However, the antibody had very weak binding activity as indicated both in Western blotting method and in immunofluorescent method. In this report, no evidence is shown of the presence of the neutralizing activity of said monoclonal antibody.

The present inventors have also obtained a monoclonal antibody (0.58) being capable of effectively neutralizing the virus by binding to the gp120 of HTLV-III$_B$ strain (Matsushita et al., J. Virology, 62, p.2107–2114, 1988). However, said 0.5β antibody can neutralize HTLV-III$_B$ strain, but not HTLV-III$_{MN}$ strain which is more popular in immunological field.

There has never been known any monoclonal antibody which can bind to the gp120 of the HTLV-III$_{MN}$ which is popular in immunological field and can substantially neutralize the virus.

BRIEF DESCRIPTION OF THE INVENTION

The present inventors have found a monoclonal antibody which can bind to the envelope antigen of HTLV-III$_{MN}$:gp120 and can substantially neutralize the virus.

An object of the invention is to provide a monoclonal antibody being capable of neutralizing HIV. Another object of the invention is to provide a hybridoma being capable of producing said monoclonal antibody. These and other objects and advantages of the invention will be apparent to those skilled in the art from the following description.

BRIEF DESCRIPTION OF THE DRAWINGS

FIGS. 4A and 4B show the reactivity of overlapping peptides (SEQ ID NOS:1–23 and 25) of multiple lengths and the monoclonal antibody µ5.5 measured by Pepscan (Peptide Scanning) method.

DETAILED DESCRIPTION OF THE INVENTION

Figure 1:
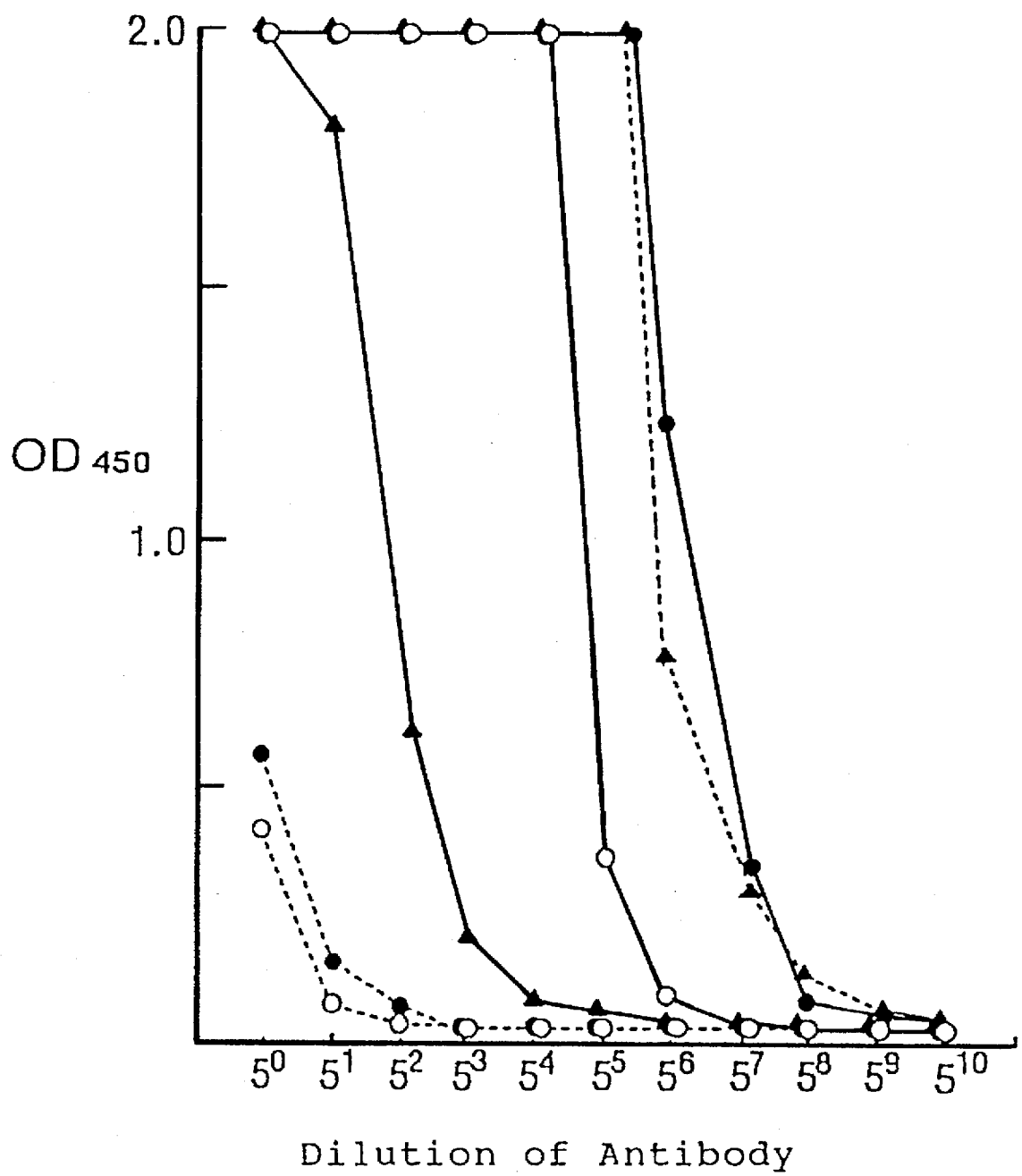
FIG. 1 shows a reactivity of the monoclonal antibodies of the invention (µ39.1 and µ5.5) to the synthetic peptides of gp120 (amino acid sequence 303–325 or 308–329) derived from the various HIV mutants. An initial concentration of each antibody is 500 µg/ml.

The term "neutralization" this disclosure means inhibition of cell free infection of HIV and also cell-to-cell infection such as syncytium formation which occurs between HIV-infected cells and non-infected cells by interaction between the gp120 and the CD4.

This invention provides a monoclonal antibody which can bind to a glycoprotein antigen having a molecular weight of about 12×10$^4$ daltons present in the envelope of HIV and can neutralize said virus, and also fragments thereof.

The monoclonal antibody of this invention can recognize the envelope glycoprotein of HTLV-III$_{MN}$ strain: gp120 and can neutralize said virus. The monoclonal antibody can be prepared by the following method.

A mammal (e.g. mouse, guinea pig, rabbit, etc.) is immunized with virus particles obtained from an appropriate HTLV-III$_{MN}$-producing cell or purified envelope glycoprotein gp120; a recombinant peptide prepared by a recombinant DNA technology, preferably a recombinant peptide corresponding to the amino acid sequence 247–370 of gp120; or a synthetic peptide prepared based on the amino acid sequence of the virus protein, preferably a synthetic peptide corresponding to the amino acid sequence 303–325 of gp120, more preferably corresponding to the amino acid sequence 309–318 of gp120. The spleen cells taken out from the thus immunized mammal is cell-fused with, for example, mouse myeloma cells to give a hybrodoma, from which cells corresponding to a purified envelope glycoprotein gp120 or the above recombinant peptide or synthetic peptide are selected, and then the cells are cultivated to give the desired monoclonal antibody.

The above preparation of hybridoma can be carried out by a method of Kohler and Milstein (Nature, 256, p.495, 1975). The virus particles or envelope glycoprotein gp120 used as the antigen include HTLV-III$_{MN}$-producing cells prepared by sucrose density-gradient centrifugation method, e.g. derived from H9/HTLV-III$_{MN}$; a recombinant peptide prepared by a recombinant DNA technology; or a synthetic peptide prepared based on the amino acid sequence of said virus protein, and further any other immunogen prepared by a conventional method. The mouse to be immunized includes BALB/c mouse, F1 mouse of BALB/c mouse and other mouse, and the like. Immunization is carried out by using an antigen of 20 to 200 µg per one mouse (4 to 8 week age, weighing 20 to 30 g), wherein the antigen is administered 3 to 6 times for every 2 to 3 weeks. The feeding of mouse and the collection of spleen cell from the immunized mouse are carried out in a conventional manner.

Myeloma cells include MOPC-21NS/1 (Nature, 256, p.495, 1975), SP2/0-Ag14 (Nature, 276, p.269, 1979), p3X63Ag8-U1 (Eur. J. Immunol., 6, p.511, 1976), p3X63-Ag8 (Nature, 256, p.495, 1975), p3X63-Ag8.653 (J. Immunol., 123, p.1548, 1979), and the like.

The spleen cells and myeloma cells are mixed in a ratio of 1:1 to 10:1 by volume, and the cell-fusion is carried out in a phosphate buffer (pH 7.2–7.4) containing NaCl (about 0.85 wt. %), dimethylsulfoxide (10–20 v/v%) and polyethylene glycol having a molecular weight of 1,000 to 6,000, by incubating the mixture at 35° to 37° C. for 1 to 5 minutes. The fused cells (hybridoma) can be collected from the base medium containing hypoxanthine (1.3–1.4 mg/dl), aminoputerin (18–20 µg/dl), thymidine (375–4,000 µl/dl), streptomycin (50–100 µg/ml), penicillin (50–100 U/ml), glutamine (3.5–4.0 g/l) and fetal bovine serum (10–20 wt. %), wherein the fused cells grow. The base medium includes any medium which is usually used for cultivation of animal cells, such as RPMI1640 medium, Eagle's MEM medium, and the like. Cloning of the fused cells is repeated at least three times by limiting dilution method.

The hybridoma is cultivated in the same manner as usually used in cultivation of animal cells, whereby the desired monoclonal antibody of this invention is produced in the medium. For example, when the hybridoma (2×10$^6$–5× 10$^6$ cells) is cultivated in RPMI1640 medium (10–20 ml) containing streptomycin (50–100 µg/ml), penicillin (50–100 U/ml), glutamine (3.5–4.0 g/l) and fatal bovine serum (10–20 wt. %) in the presence of 5% CO$_2$ in a flask at 35°–37° C. for 3 to 7 days, whereby the antibody is secreted and accumulated in the medium. The hybridoma may also be grown by injecting intraperitoneally into a nude mouse or BALB/c mouse treated with pristane, whereby the antibody is accumulated within the ascites. That is, pristane (0.5–1 ml) is intraperitoneally inoculated into the mouse, and two to three weeks after the inoculation, the hybridoma (5×10$^6$–1×10$^7$ cells) is intraperitoneally transplanted thereto. After 7 to 10 days, accumlated ascites are collected. The monoclonal antibody contained in the culture medium or the ascites can be isolated by affinity chromatography with Affigel Protein A MAPS-II kit (BIO-RAD) or by any other conventional method.

The monoclonal antibody thus obtained can recognize an epitope on gp120 derived from HTLV-III$_{MN}$ strain and can effectively neutralize the virus but does not bind to other HTLV-III strains. The monoclonal antibody has the following characteristics:

(a) immunoglobulin class: IgG, κ, (b) specifically binds to glycoprotein antigen having a molecular weight of 12×10$^4$ daltons (gp120) of HTLV-III$_{MN}$, (c) specifically binds to an epitope which is present in the region represented by the amino acid sequence 303 to 325 (Tyr Asn Lys Arg Lys Arg Ile His Ile Gly Pro Gly Arg Ala Phe Tyr Thr Thr Lys Asn Ile Ile Gly) of gp120 of HTLV-III$_{MN}$, SEQ ID NO:24, (d) specifically binds to the surface of HTLV-III$_{MN}$ viral particles and thereby inhibits the infection to CD4-positive cells by HTLV-III$_{MN}$, and (e) specifically binds to the surface of cells infected with HTLV-III$_{MN}$ and thereby inhibits the syncytium formation induced by interaction between the infected cells and uninfected cells as determined by in vitro inhibition of syncytium formation.

The monoclonal antibody of the present invention, more particularly, specifically binds to an epitope which is present in the region represented by the amino acid sequence 309 to 318 (Ile His Ile Gly Pro Gly Arg Ala Phe Tyr SEQ ID NO:25) of gp120 of HTLV-III$_{MN}$.

Thus, the monoclonal antibody of this invention can clearly inhibit the cell-to-cell infection such as syncytium formation and/or cell-free virus infection such as infection with HTLV-III$_{MN}$. Accordingly, the monoclonal antibody can be used for the prophylaxis and treatment of AIDS. Moreover, the monoclonal antibody of this invention is also useful for the inhibition of growth of AIDS virus in human host. Besides, since the monoclonal antibody of this invention has a strong neutralizing activity against HTLV-III$_{MN}$, it is also effective for the prevention of infection of the virus to uninfected T cells.

A representative example of the hybridoma being capable of producing the monoclonal antibody of this invention has been deposited to Fermentation Research Institute, Agency of Industrial Science and Technology, Tsukuba, Japan under Budapest Treaty in accession No. FERM BP-3402 on Feb. 10, 1990.

This invention is illustrated by the following Examples but should not be construed to be limited thereto.

EXAMPLE 1

Preparation of monoclonal antibody:

Preparation of antigen (1) A synthetic peptide:

A synthetic peptide corresponding to the amino acid sequence 303 to 325 of the envelope glycoprotein gp120 of HTLV-III$_{MN}$ (Tyr Asn Lys Arg Lys Arg Ile His Ile Gly Pro Gly Arg Ala Phe Tyr Thr Thr Lys Ash Ile Ile Gly SEQ ID NO:24) is used as an immunogen and an antigen for assay.

The above peptide is prepared with ABI430A Peptide Synthesizer (Applied Biosystem). The crude peptide thus prepared is removed from the substrate resin by TFMSA method (Yanaihara, C., Experimental Medicine, 6, No. 10, p.141–148, 1988) and purified by reverse phase high performance liquid chromatography (HPLC). The purification by reverse phase HPLC is repeated three times and the fractions containing the product are collected, and the product is subjected to amino acid analysis, by which it is confirmed that the amino acid sequence of the product corresponds well to that of HTLV-III$_{MN}$ strain, and thereby it is concluded that the product is a synthetic peptide of gp120 of HTLV-III$_{MN}$ strain.

The thus-obtained synthetic peptide (designated "SP-1") is lyophilized, and then is bound to an immunization carrier, KLH (Keyhole Limpet Hemocyanin) to give a peptide-KLH conjugate in the following manner.

That is, the above peptide SP-1 (10 mg) is dissolved in 10 mM phosphate buffered saline (PBS, pH 7.0, 2 ml), and thereto is added a solution of MBS crosslinking agent in dimethylformamide (40 mg/100 μl), and the mixture is stirred at room temperature for 30 minutes. The reaction mixture is washed with dichloromethane (2 ml) three times, and the aqueous layer (designated "Solution A") is separated.

Separately, KLH (20 mg) is dissolved in 0.2M Tris-HCl buffer (pH 8.6, 8M urea, 5 ml) and thereto is added dithiothreitol (DTT), and the mixture is stirred at room temperature for one hour. To the reaction mixture is added 10% trichloroacetic acid (3 ml), and the resulting precipitate is separated by filtration with suction, washed with distilled water (2 ml) and then dissolved in 20 mM sodium phosphate buffer (NaPB, pH 7.0, 0.6M urea, 5 ml) to give a solution (Solution B).

The above Solution A and Solution B are mixed and stirred at room temperature for 3 hours, and the reaction product is dialyzed and lyophilized.

The synthetic peptide of gp120 of HTLV-III$_{MN}$ strain and peptide-KLH conjugate prepared above are used as an immunogen and antigen for assay.

(2) Cultivation of HTLV-III$_{MN}$-producing cells and preparation of HTLV-III$_{MN}$ particles:

H9/HTLV-III$_{MN}$ strain is used as HTLV-III$_{MN}$-producing cells. A culture medium is RPMI 1640 supplemented with 20% FCS and 2 mM L-glutamine to be used in a 50 L scale. The H9/HTLV-III$_{MN}$ strain is cultivated in said culture medium in a 36 liter Spinner flask with a cultivation controller (manufactured by Wakenyaku Kogyo K.K.) and the resulting cells-floating mixture is centrifuged at 3,000 r.p.m. for 5 minutes to separate the culture supernatant. The culture supernatant is subjected to sucrose density-gradient centrifugation (25%, 50%, discontinuing, 89,000×g, 20 hrs.) with a continuous rotater (RPC35T, manufactured by Hitachi Ltd.) at a rate of 2 liter/hr. to separate viral particles, wherein the viral particles are collected in 30–45% sucrose layer. The viral particles thus obtained are used as an immunogen and an antigen for assay.

Purified gp120 is prepared by collecting the cells from the above H9/HTLV-III$_{MN}$ culture broth by centrifugation, lysing the cells with 1% Triton X-100, centrifuging the mixture and then purifying the supernatant by affinity chromatography with ConA—Sepharose 4B column. The eluted solution is further purified by affinity chromatography with HIV antibody (IgG)—Sepharose 4B column. The purified gp120 thus obtained is used as an immunogen and an antigen for assay.

(3) Preparation of recombinant expression peptide of HTLV-III$_{MN}$ gp120 V3 domain:

H9/HTLV-III$_{MN}$ cells ($10^6$–$10^7$ cells) are floated in 1×RSB buffer and thereto are added sodium dodecylsulfate (SDS, at final concentration of 1%) and Proteinase K (at final concentration of 1 mg/ml), and the mixture is incubated at 37° C. for 2 hours. The resulting mixture is repeatedly subjected to extraction with phenol and precipitation with ethanol to give a high molecular weight DNA (genomic DNA). HTLV-III$_{MN}$ gp120 V3 domain (amino acid 247–370) is amplified by conventional PCR method by using a template of the above high molecular weight DNA and the following A primer (SEQ ID NO:26) and C primer (SEQ ID NO:27):

| | |
|---|---|
| A primer: | (5')TGTACACATGGAATTAGGCCAG(3') |
| C primer: | (3')GAAGTCCTCCCCTGGGTCTTTA(5') |

The amplification is carried out with Taq polymelase for 30 to 35 cycles.

The amplified DNA fragment is cloned with pUC18 plasmid, and the cloned DNA fragment is inserted into pUEX2 expression vector (manufactured by Amersham, code No. RPN1515; Bressan, G. and Stanley, Y., Nucleic Acid Research, 15, p.10056, 1987). *Escherichia coli* is transfected with the expression vector and then subjected to heat induction at 42° C. to express the peptide. The expressed HTLV-III$_{MN}$ gp120 V3 domain (amino acid 247-370) is a fusion protein with β-galactosidase, which is then purified in the form of *E. coli*-inclusion body as follows.

After expression, *E. coli* is fractured with glass beads and treated with lysozyme (final concentration, 0.1 mg/ml) at 4° C. The resulting precipitate separated by centrifugation is treated with Triton X-100 (final concentration, 0.5%). The precipitate is solubilized with 8M urea and is used as an immunogen and an antigen for assay.

Immuno-sensitization of mouse

An example of immuno-sensitization of mouse with the synthetic peptides prepared hereinabove is illustrated below.

BALB/c mice (4–8 weeks age) are inoculated with the synthetic peptide and synthetic peptide-KLH conjugated antigen mixture (each 100 μg) three times in intraperitoneal route and one time in intravenous route, on the first day i.p. in the presence of Freund's complete adjuvant, on 14th day i.p. in the presence of Freund's incomplete adjuvant, on 28th day i.p. in the presence of Freund's incomplete adjuvant, and on 42nd day i.v. in the absence of an adjuvant.

Cell fusion and cultivation of hybridoma

Three days after the immunization, the spleen cells are collected from the mice in a usual manner.

The spleen cells are mixed with myeloma cells p3X63Ag8-U1 in a ratio of cells of 1:5, and the mixture is centrifuged (1,200 r.p.m./5 minutes) to remove the supernatant. The precipitated mass of cells is well untangled and is added to a mixture (1 ml) of polyethylene glycol-4000 (2 g), minimum essential medium (MEM) (2 ml) and dimethysulfoxide, and the mixture is incubated at 37° C. for 5 minutes, and thereto is slowly added MEM so as to be total volume 50 ml. The mixture is centrifuged (900 r.p.m./5 minutes) to remove the supernatant fluid and the cells are untangled mildly. To the cells is added a normal medium (RPMI1640 medium with 10% FCA) (100 ml), and the cells are gradually suspended therein with a measuring pipette.

The suspension is poured into each well of a 24-well culture plate (1 ml/well) and the plate is incubated in an incubator containing 5% $CO_2$ at 37° C. for 24 hours. Then, 1 ml/well of HAT medium [a normal medium supplemented with hypoxanthine ($1\times10^{-4}$M), thymidine ($1.5\times10^{-3}$M) and aminopterin ($4\times10^{-7}$M)] is added and the plate is incubated for additional 24 hours. The culture is continued for 10 to 14 days in the same manner while exchanging the culture supernatant (1 ml) with the same volume of a HT medium (HAT medium depleted with aminopterin) every 24 hours for 2 days.

Each well with the fused cells (about 300 cells) growing in a colonial shape is selected. The culture supernatant (1 ml) of the selected well is exchanged with the same volume of the HT medium and then the exchange is repeated every 24 hours for 2 days.

After 3 to 4 day culture with the HT medium, a part of the culture supernatant is collected and used for selection of the desired hybridoma by screening method as described hereinbelow.

Screening of hybridoma

The desired hybridoma is selected by a combination of enzyme immunoassay (EIA), immunofluorescence and Western blotting methods. The thus selected clone is measured for its neutralizing activity.

(1) EIA:

To each well of a 96-well microtest plate is added 100 μl/well of the synthetic peptide antigen, purified gp120 antigen, or recombinant peptide (protein concentration: 2 μg/ml), prepared as mentioned above, and the plate is incubated at 4° C. overnight for immobilization. Then, 2% bovine serum albumin (BSA) solution (100 μl) is added to each well and the plate is incubated in the same manner for masking. To each well of the thus prepared antigen-immobilized plate are added the hybridomas obtained by the cell fusion and the culture supernatant of hybridomas after cloning and the plate is incubated at 37° C. for 2 hours. The plate is washed with 0.1% Tween 20/PBS three times and 100 μl/well of a solution of peroxidase-labelled anti-mouse immunoglobulin (manufactured by Cappel, ×5,000 dilution). After incubation at 37° C. for 1 hour, the plate is washed with 0.1% Tween 20/PBS five times. Then, a substrate solution of 3,3',5,5'-tetramethylbenzidine (TMBZ) is added to each well for color development and an optical density is measured at 450 nm. A hybridoma clone is thus selected which strongly reacts only with the synthetic peptide derived from HTLV-$III_{MN}$ but not with the synthetic peptide derived from HTLV-$III_B$.

(2) Immunofluorescence:

H9/HTLV-$III_{MN}$ cells or uninfected H9 cells ($5\times10^5$ cells) suspended in the culture supernatant to be tested (100 μl) are cultured at 4° C. for 30 minutes. The cultured cells are washed twice with a PBS solution containing BSA (2% and azide (0.1%) (PBS-BSA-Az). After washing, 100 μl of anti-mouse IgG labelled with fluorescein-isothiocyanate (FITC) (manufactured by Sigma, diluted to 1:40 with PBS-BSA-Az) and the mixture is reacted at 4° C. for 30 minutes. The reaction mixture is washed with PBS-BSA-Az three times and then fixed with PBS containing 0.1% paraformaldehyde.

Using a laser flow-cytometry (Spectrum III manufactured by Ortho Diagnostics), the reactivity of the antibody is measured based on the strength of fluorescence. A hybridoma showing a maximum binding ability to the surface of H9/HTLV-$III_{MN}$ cells is selected and cloned by limiting dilution method. The hybridoma clone after cloning is also selected in the same manner.

(3) Western blotting:

Western blotting is carried out in accordance with Towbin et al. [Proc. Natl. Acad. Sci. U.S.A., 76, p 4350 (1979)].

A purified HTLV-$III_{MN}$ virus is prepared by the method described in the literature [Science, 224, p.497 (1984)] and electrophoresed by 12% sodium dodecyl sulfate-polyacrylamide gel electrophoresis (SDS-PAGE). The gel is then transferred to nitrocellulose membrane to transfer the virus to the membrane and the membrane is cut into strips with 0.4 to 0.5 cm width. Each strip is immersed in a hybridoma culture supernatant and incubated at room temperature overnight. After washing with PBS three times, each strip is warmed in a solution of biotin-labelled anti-mouse IgG (manufactured by TAGO) diluted to 1:750. After washing with PBS three times, each strip is immersed in a solution of horseradish peroxidase-conjugated avidin (manufactured by Sigma) diluted to 1:1000 and warmed for 1 hour. After washing with PBS three times, a coloring reagent containing 4-chloro-1-naphthol (manufactured by Bio-Rad) is used for color development. A hybridoma showing a colored band of HTLV-III$_{MN}$ gp120 is selected and cloned. The hybridoma clone after cloning is also selected in the same manner.

(4) Measurement of neutralizing activity:

The culture supernatant of H9/HTLV-III$_{MN}$ is used as an original viral solution ($10^{4.5}$ to $10^5$ TCID$_{50}$).

The viral solution adjusted to 10 TCID$_{50}$/50 µl and 50 µl of the hybridoma clone culture supernatant or purified ascites, which are diluted in series, are inoculated into each well of a 96-well flat-bottomed plate and the plate is incubated at 37° C. for 1 hour. Then, MT4 cells are added to each well at $10^4$ cells/100 µl/well, said cells being floated in RPMI 1640 medium supplemented with 10% FCS, L-glutamine (3.5 to 4.0 g/l), penicillin (50 U/ml) and streptomycin (50 g/ml), and cultured at 37° C. for 5 days.

The neutralizing activity is evaluated based on an ability of the antibody to inhibit the syncytium formation observed during infection. The neutralization titer is expressed as a minimum effective concentration of the antibody showing 100% inhibition of syncitium formation.

The above selection procedure provides hybridomas (µ39.1 and µ5.5) capable of producing the desired monoclonal antibody.

Preparation of monoclonal antibodies with hybridomas µ39.1 and µ5.5:

Each 5×10$^6$ cells/animal of the hybridoma µ39.1 or µ5.5 obtained above is intraperitoneally administered to pristane-treated female BALB/c mice (8 weeks age). After 10 to 21 days, ascites cancer is induced. Ascites are taken out from the mice and centrifuged at 3,000 rpm for 5 minutes to remove solid components. Then, the antibody is purified by subjecting the supernatant to affinity chromatography using Affigel Protein A MAPS-II Kit (manufactured by Bio-Rad).

EXAMPLE 2

Analysis of monoclonal antibodies µ39.1 and µ5.5

(1) Reactivity to gp120 synthetic peptide derived from various HIV mutants:

Synthetic peptides of gp120 (amino acid sequence 303-325 or 308-329) derived from HTLV-III$_{MN}$, HTLV-III$_B$, HTLV-III$_{RF}$, and HIV-2 are employed. The reactivity is tested in the same manner as described in the above Screening of hybridoma, (1) EIA.

As shown in FIG. 1, it is clear that the control 0.56 antibody strongly reacts with the peptide derived from HTLV-III$_B$ but not with the peptide derived from HTLV-III$_{MN}$ at a lower concentration although it cross-reacts with the peptide derived from HTLV-III$_{MN}$ at a higher concentration.

On the other hand, it is seen that the monoclonal antibody µ39.1 is a HTLV-III$_{MN}$-specific antibody which strongly reacts with the peptide derived from HTLV-III$_{MN}$. It is also seen that the µ39.1 monoclonal antibody reacts neither with the synthetic peptides derived from HTLV-III$_{RF}$ nor with those from HIV-2 (data is not shown in FIG. 1).

The reactivity of the monoclonal antibody µ5.5 is completely the same as that of µ39.1, i.e. this monoclonal antibody is a HTLV-III$_{MN}$-specific antibody which strongly reacts only with the peptide derived from HTLV-III$_{MN}$.

(2) Reactivity to gp120 derived from infected cells (Western blotting):

In order to determine the reactivity of the monoclonal antibodies µ39.1 and µ5.5 to the external envelope glycoprotein gp120 derived from infected cells, Western blotting technique is used. An antigen used is an H9/HTLV-III$_{MN}$ cell lysate. The procedure described in the above Screening of hybridoma, (3) Western blotting is repeated.

Figure 2:
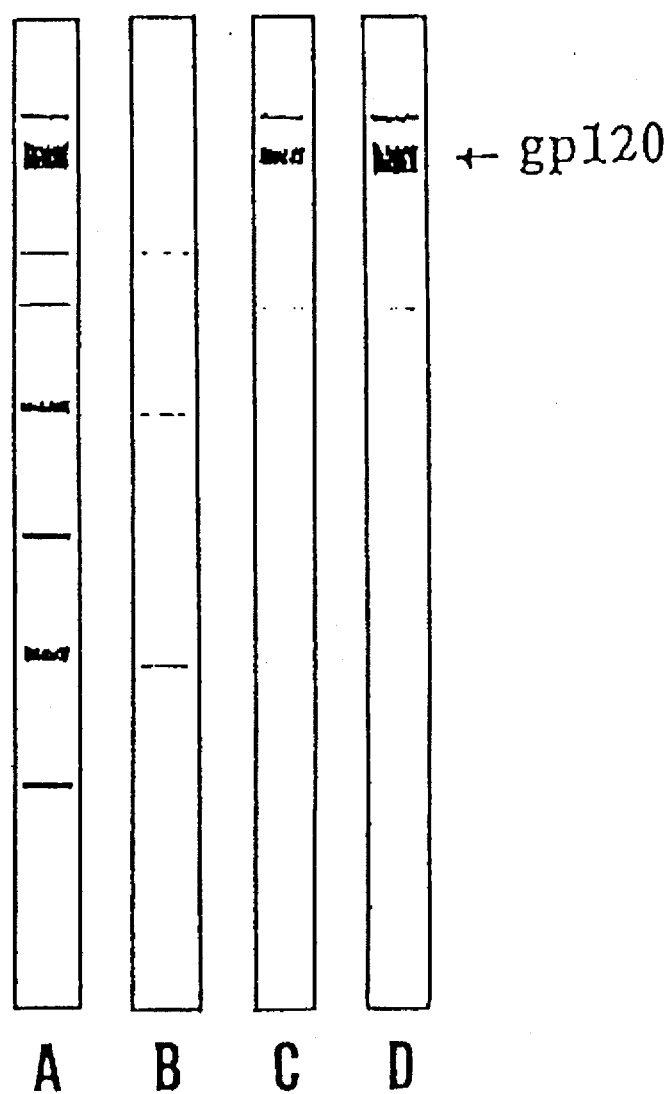
FIG. 2 shows a reactivity of the monoclonal antibodies of the invention (µ39.1 and µ5.5) to the external envelope glycoprotein gp120 derived from the HTLV-III$_{MN}$-infected cells.

As shown in FIG. 2, strip A is a positive control in which HIV antibody positive human serum is employed, wherein a gp120 band is observed. The monoclonal antibody 0.5β does not react with gp120 derived from HTLV-III$_{MN}$ (strip B) while the monoclonal antibodies µ39.1 and µ5.5 recognize gp120 derived from HTLV-III$_{MN}$ (strips C and D). It is also found that the reactivity of the monoclonal antibody µ5.5 is stronger than that of the monoclonal antibody µ39.1 as shown in FIG. 2.

(3) Neutralizing property of monoclonal anbibodies µ39.1 and µ5.5:

The neutralizing property of the monoclonal antibodies µ39.1 and µ5.5 is examined according to the procedure described in the above Screening of hybridoma, (4) measurement of neutralizing activity. The results are shown in the following Table 1.

TABLE 1

| Virus | Inhibitory activity on cell to cell infect. by infected cells[1] | | | Virus-neutralizing activity[2] | | |
|---|---|---|---|---|---|---|
| | MoAb | | | | | |
| | µ5.5 | µ39.1 | 0.5β | µ5.5 | µ39.1 | 0.5β |
| III$_{MN}$ | 16 | 63 | >500 | 1 | 63 | >500 |
| III$_B$/LAV | >500 | >500 | 31 | >500 | >500 | 4 |
| III$_{RF}$ | >500 | >500 | >500 | >500 | >500 | >500 |

(Note):
[1]Minimum effective concentration (µg/ml) of the antibody showing 80% inhibition of cell to cell infection by infected cells
[2]Minimum effective concentration (µg/ml) of the antibody showing 100% inhibition of viral infection The right column in Table 1 shows a minimum effective concentration of the antibody showing 100% inhibition of infection of each variant viral species. The control monoclonal antibody 0.5β shows a neutralizing activity specific to HTLV-III$_B$/LAV. On the other hand, the monoclonal antibody µ39.1 is a monoclonal antibody capable of specifically neutralizing HTLV-III$_{MN}$ which inhibits the infection of HTLV-III$_{MN}$ totally (100%) at a concentration of 63 µg/ml but not the infection of the other HTLV strains III$_B$ and III$_{RF}$. The monoclonal antibody µ5.5, likewise µ39.1, shows a neutralizing activity sepecific to the strain III$_{MN}$. It is seen that the neutralizing activity of the monoclonal antibody μ5.5 is more than 50 times higher than that of μ39.1 and is a strong neutralizing antibody which inhibit the infection of the strain $III_{MN}$ totally (100%) at a concentration of 1 μg/ml.

The left column of Table 1 indicates a minimum effective concentration of the antibody showing 80% inhibition of cell to cell infection by infected cells. The control monoclonal antibody 0.5β shows a neutralizing activity specific to $III_B$/LAV infected cells. On the other hand, the monoclonal antibody μ39.1 inhibits the cell to cell infection by $III_{MN}$ infected cells at a concentration of 63 μg/ml but not the infection by $III_B$ or $III_{RF}$ infected cells. That is, it is found that the monoclonal antibody μ39.1 is a neutralizing antibody specific to the strain $III_{MN}$ in the cell to cell infection by the infected cells.

The monoclonal antibody μ5.5, likewise μ39.1, also shows a neutralizing activity specific to the strain $III_{MN}$. It is seen that the neutralizing activity of the monoclonal antibody μ5.5 is more than about 4 times higher than that of μ39.1 and is a strong neutralizing antibody which inhibit the cell to cell infection by the infected cells at a concentration of 16 μg/ml.

EXAMPLE 3

Preventive effect of the monoclonal antibody μ5.5 on HTLV infection in mice with human peripheral blood lymphocyte (hu-PBL-SCID mice)

$2\times10^7$ cells of human peripheral blood lymphocyte (PBL) having no infection with EB virus were administered to the peritoneal of severe complex immunodeficiency mice (SCID mice) of 7 to 15 weeks old. After 2 to 3 weeks, HTLV-$III_{MN}$ strain ($5\times10^2$ $TCID_{50}$) and the neutralizing antibody of the present invention (μ5.5; 360 mg/kg) were simultaneously administered into the peritoneal of the SCID mice with human PBL. Each three mice were employed for the group that received the antibody of the invention and for the group that received no antibody.

Four days after the final administration, peripheral blood lymphocytes (PBL), peritoneal lavage cells and spleen were taken out, and the HTLV-$III_{MN}$ gene was detected and quantified by Polymerase Chain Reaction (PCR) method.

First, each of cells were floated in RSB buffer, thereto added SDS (final concentration 1%) and Proteinase K (final concentration 1 mg/ml), and the mixture was incubated at 37° C. for 2 hours. Thereafter, the procedures of phenol extraction and ethanol precipitation were repeated to give a high molecular weight DNA (genomic DNA). Using this high molecular weight DNA as a template, the gag region of HTLV-$III_{MN}$ was amplified by the PCR method with the following SK38/39 gag primers, followed by acrylamide gel electrophoresis. The gel after the electrophoresis was transferred to a nylon membrane, to which $^{32}$P-labelled SK19 gag probe was hybridized to conduct autoradiography.

Figure 3:
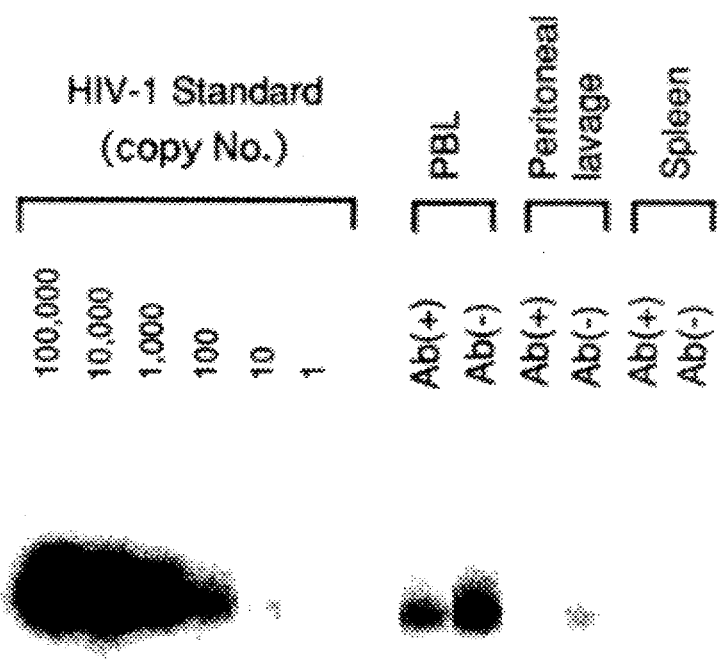
FIG. 3 shows a protective effect of the monoclonal antibody µ5.5 on HTLV infection in mice with human peripheral blood lymphocyte (hu-PBL-SCID mice).

The results are shown in FIG. 3. In each of mouse PBL, peritoneally exudated cells and spleen, the group that received the administration of μ5.5 antibody of the present invention exhibited inhibition of HTLV-$III_{MN}$ viral infection (reduction in an amount of detected viral genes) as compared to the group that received no antibody, which proves the protective effect of the antibody of the present invention on viral infection.

Spleen-derived cells ($1\times10^6$ cells) were also cultured under stimulation with phytohemagglutinin (PHA) for 3 days and an amount of HTLV core antigen (p24) in the supernatant was measured. As a result, said p24 antigen (110 pg/ml) was detected in the group that received no antibody whereas the group that received the antibody remained negative (the amount of the p24 antigen: 10 pg/ml), which also proves the protective effect of the neutralizing antibody of the present invention on viral infection.

EXAMPLE 4

Analysis of epitope that is recognized by the monoclonal antibody μ5.5

The V3 synthetic peptide antigen derived from HTLV-$III_{MN}$ strain used as an immunogen in the present invention has an amino acid sequence of YNKRKRIHIGPGRAFYT-TKNIIG (23 amino acids SEQ ID NO:24). The μ5.5 monoclonal antibody of the present invention has been confirmed to react with the above 23 amino acid sequence. In order to determine which portion of this sequence the monoclonal antibody of the present invention recognizes, Epitope Analysis Method (Epitope Scanning Kit; Chiron Mimotopes Pty Ltd.) was used.

Overlapping peptides comprising 7 to 15 sequential amino acids from the above 23 amino acid sequence (i.e. a series of peptides having 7 to 15 sequential amino acids wherein each one amino acid is shifted from the N-terminus towards the C-terminus in each set of peptides) were synthesized on a polystyrene rod. The reactivity of these peptides with the μ5.5 monoclonal antibody of the present invention was investigated by EIA for determining which portion of the 23 amino acid sequence is an epitope. As a result, it was found that the μ5.5 monoclonal antibody of the present invention well reacted with peptides having at least 10 amino acids and containing IHIGPGRAFY (SEQ ID NO:25) but did not reacted peptides having less than 10 amino acids at all (data are shown in FIG. 4 SEQ ID NOS:1–23 and 25). From this, the ten amino acid sequence IHIGPGRAFY (SEQ ID NO:25) was found to be an essential epitope of the synthetic peptide which is recognized by the monoclonal antibody of the present invention.

---

SK38 (SEQ ID NO: 28); (5')ATAATCCACCTATCCCAGTAGGAGAAAT(3')
SK39 (SEQ ID NO: 29); (5')TTTGGTCCTTGTCTTATGTCCAGAATGC(3')
SK19 (SEQ ID NO: 30); (5')ATCCTGGGATTAAATAAAATAGTAAGAATGTATAGCCCTAC(3')

What is claimed is:

1. A murine monoclonal antibody which is produced by the hybridoma FERM BP-3402 and which is capable of neutralizing human T-lymphotropic virus $III_{MN}$ (HTLV-$III_{MN}$) and has the following characteristics:

(a) immunoglobulin class: IgG, K, (b) specifically binds to an epitope which is present in the region represented by the amino acid sequence 303 to 325 (Tyr Ash Lys Arg Lys Arg Ile His Ile Gly Pro Gly Arg Ala Phe Tyr Thr Thr Lys Asn Ile Ile Gly) of a glycoprotein antigen having a molecular weight of about $12 \times 10^4$ daltons of gp120 of HTLV-$III_{MN}$, SEQ ID NO:1, (c) specifically binds to the surface of HTLV-$III_{MN}$ viral particles and thereby inhibits the infection of CD4-positive cells by HTLV-$III_{MN}$, (d) specifically binds to the surface of cells infected with HTLV-$III_{MN}$ and thereby inhibits the syncytium formation induced by interaction between the infected cells and uninfected cells as determined by in vitro inhibition of syncytium formation, and (e) does not bind to any HTLV-III strain other than HTLV-$III_{MN}$, or an antigen-binding fragment thereof.

* * * * *